(12) United States Patent
Sanz et al.

(10) Patent No.: US 8,901,367 B2
(45) Date of Patent: Dec. 2, 2014

(54) END SEAL FOR AN ABSORBENT ARTICLE

(75) Inventors: Miguel Brandt Sanz, Wachtberg (DE); Peter Dziezok, Hochheim (DE); Ralf Geilich, Eppstein (DE); Carson Heinrich Kreuzer, Suizbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 1271 days.

(21) Appl. No.: 11/329,797

(22) Filed: Jan. 11, 2006

(65) Prior Publication Data

US 2006/0155254 A1 Jul. 13, 2006

(30) Foreign Application Priority Data

Jan. 11, 2005 (EP) ................... 05000392

(51) Int. Cl.
*A61F 13/15* (2006.01)
*A61F 13/539* (2006.01)

(52) U.S. Cl.
CPC ......... *A61F 13/15203* (2013.01); *A61F 13/539* (2013.01)
USPC .......................................... 604/367; 604/378

(58) Field of Classification Search
USPC .............................. 604/385.01–402, 367–370
See application file for complete search history.

(56) References Cited

U.S. PATENT DOCUMENTS

| | | | |
|---|---|---|---|
| 3,860,003 A | 1/1975 | Buell | |
| 3,929,135 A * | 12/1975 | Thompson | 604/385.08 |
| 4,573,986 A | 3/1986 | Minetola et al. | |
| 4,704,115 A * | 11/1987 | Buell | 604/385.26 |

(Continued)

FOREIGN PATENT DOCUMENTS

| | | |
|---|---|---|
| DE | 10002149 A1 | 7/2001 |
| EP | 0172035 A | 2/1986 |

(Continued)

OTHER PUBLICATIONS

English translation of JP 2004-141257 to Yasushi et al.*

(Continued)

*Primary Examiner* — Melanie Hand
(74) *Attorney, Agent, or Firm* — Charles R. Ware; Christian M. Best

(57) ABSTRACT

The present invention relates to absorbent articles, such as diapers and sanitary napkins, and cores useful for such articles. More specifically, the invention relates to an absorbent article having a longitudinal centerline and a transverse centerline, the absorbent article comprising an absorbent core, the core comprising a storage layer and a wearer facing side oriented towards a wearer when the article is being worn and an opposed garment facing side, the absorbent article further comprising a liquid pervious topsheet on the wearer facing side of the core and a liquid pervious backsheet on the garment facing side of the core, the core further comprising a first core wrap sheet covering the wearer facing side of the storage layer and a second core wrap sheet covering the garment facing side of the storage layer the first core wrap sheet being joined to the second core wrap sheet along at least one transverse stripe of juncture, wherein the stripe of juncture covers a total area and the stripe of juncture provides a bond strength of at least 1 N/cm between the first core wrap sheet and a second core wrap sheet as measured as tensile strength in the longitudinal direction and wherein the stripe of juncture comprises an open area of at least 20% of the total area.

19 Claims, 3 Drawing Sheets

(56) References Cited

U.S. PATENT DOCUMENTS

| | | | |
|---|---|---|---|
| 4,834,735 A | 5/1989 | Alemany et al. | |
| 5,037,416 A | 8/1991 | Allen et al. | |
| 5,151,092 A | 9/1992 | Buell et al. | |
| 5,269,775 A | 12/1993 | Freeland et al. | |
| 5,458,592 A * | 10/1995 | Abuto et al. | 604/378 |
| 5,462,538 A * | 10/1995 | Korpman | 604/372 |
| 5,569,234 A | 10/1996 | Buell et al. | |
| 5,625,222 A | 4/1997 | Yoneda et al. | |
| 5,885,681 A | 3/1999 | Korpman | |
| 6,004,306 A | 12/1999 | Robles et al. | |
| 6,437,214 B1 * | 8/2002 | Everett et al. | 604/378 |
| 6,717,028 B1 | 4/2004 | Oberstadt | |
| 2004/0122404 A1 * | 6/2004 | Meyer et al. | 604/385.19 |
| 2004/0162536 A1 | 8/2004 | Becker | |
| 2004/0265529 A1 * | 12/2004 | Luhmann et al. | 428/40.1 |
| 2006/0155253 A1 | 7/2006 | Dziezok | |

FOREIGN PATENT DOCUMENTS

| | | |
|---|---|---|
| EP | 0570016 A | 11/1993 |
| EP | 0847263 A1 | 6/1998 |
| EP | 0951884 A1 | 10/1999 |
| EP | 1088537 A2 | 4/2001 |
| EP | 0847263 B1 | 1/2002 |
| EP | 0926287 B1 | 10/2003 |
| JP | 06-063023 U | 9/1994 |
| JP | 2001-161748 A2 | 6/2001 |
| JP | 2004-141257 A2 | 5/2004 |
| WO | WO0064396 A1 | 11/2000 |

OTHER PUBLICATIONS

PCT International Search Report.

Written Opinion, PCT/US2006/000649, date of mailing Jul. 4, 2006.

* cited by examiner

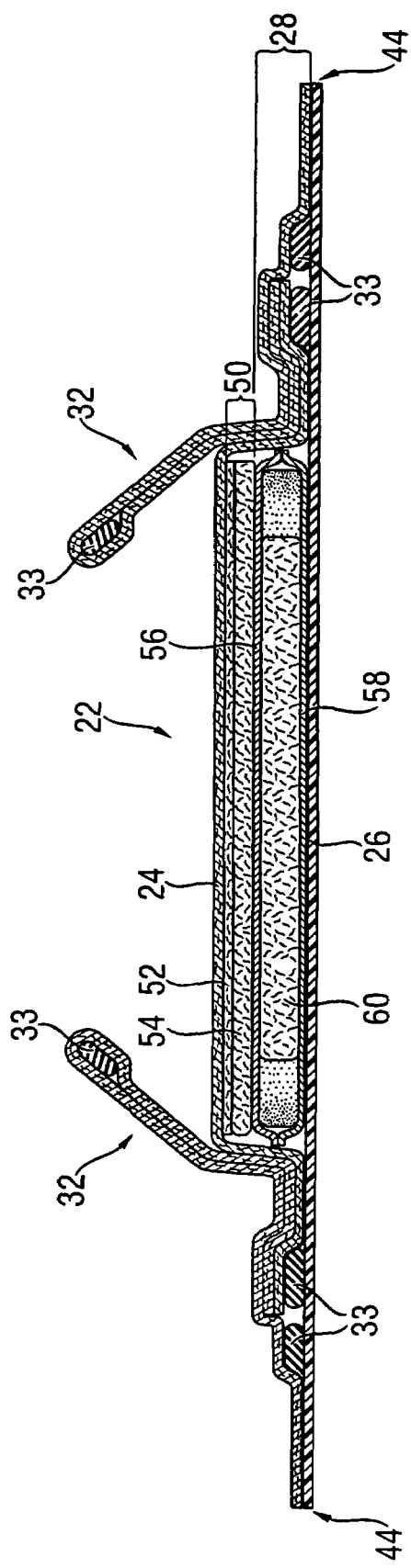

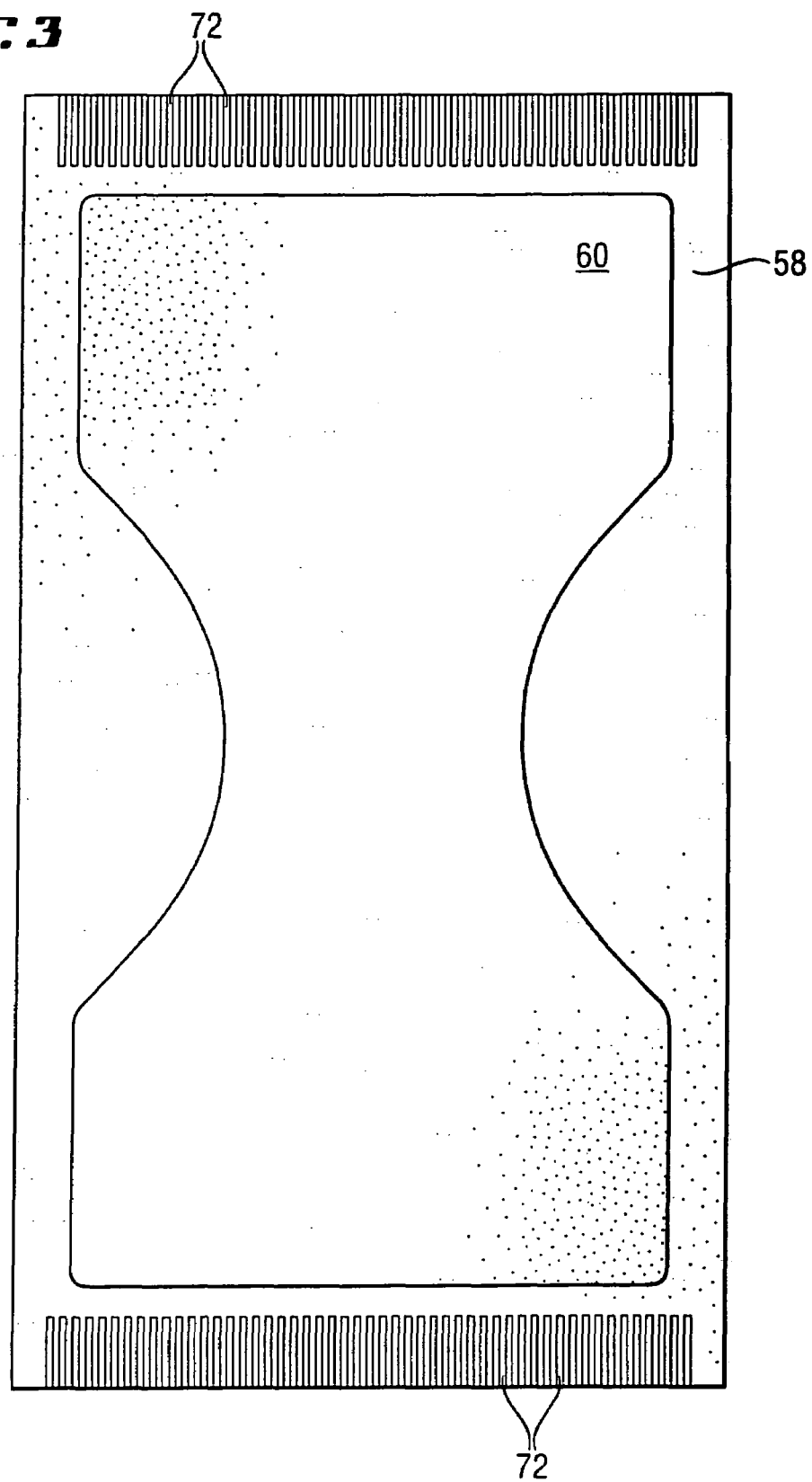

END SEAL FOR AN ABSORBENT ARTICLE

FIELD OF THE INVENTION

The present invention relates to absorbent articles, such as diapers and sanitary napkins, and cores useful for such articles. More specifically, the present invention relates to absorbent cores for such articles and the enveloping of such cores.

BACKGROUND OF THE INVENTION

Disposable absorbent articles are broadly available and consumers are used to a high performance for the collecting and retaining of menses (in the case of sanitary napkins or panty liners) or for the collecting and retaining urine and fecal material (in the case of e.g. disposable diapers). From such articles consumers expect a superior absorbency behaviour and at the same time expect excellent the wearing comfort and the dryness when being worn.

Often, such articles comprise multiple absorbent members, at least one member being primarily designed to store liquid, and at least one other member primarily designed to acquire and/or distribute liquid, the members typically being encapsulated between a topsheet (on the wearer facing side) and a backsheet (on the garment facing side).

In modern absorbent articles the absorbent core will typically comprise a super-absorbent material in combination with a fibrous material, for example cellulose. In particular, the storage layer will be provided from a combination of such materials. It is important to maintain the integrity of such absorbent core, both when the article is dry and when the article is wet, that means before use and in use. It is also important to prevent the escape of any of the absorbent materials providing the core, in particular the escape of super-absorbent materials, which are often provided in the form of particles. The escape of super-absorbent materials from the core could ultimatively lead to contact of such super-absorbent materials with the skin of the wearer. This phenomenon is known as gel on skin (as the super-absorbent materials are often also referred to as hydrogels). However, such gel on skin occurrences are considered undesirable as many consumers consider the skin contact of such super-absorbent material to be unpleasant. Some recent absorbent articles, especially disposable diapers, employ relatively open topsheet structures. These open topsheets promote the absorbance or at least the adherence of high viscosity exudates, such as bowel movement. However, when it's specifically comes to gel on skin problems, these open topsheet structures present a challenge, as they do not represent a highly effected barrier for super-absorbent particles, which may escape from the absorbent core of the absorbent article.

U.S. Pat. No. 4,573,986 (filed in 1984) discloses an early attempt for obviating lifting out of fibers and particulate matters from the absorbent core of an absorbent garment. A wet-strength-tissue envelope is disclosed in which the absorbent core is disposed and secured. The wet-strength-tissue paper or a similar laminate is secured in face to face relation with the core by an open pattern of adhesive, which may, for example, comprise a fine pattern of globulettes of adhesive. Alternatively, a reticulated network of filaments of adhesives can be used.

EP 847 263 (filed in 1995) discloses a more recent core wrap material: Disclosed is a core wrap made from a fibrous non-woven web, preferably a polypropylene melt-blown non-woven material. This core wrap material may be folded over on itself and then sealed using, for example, adhesives, heat and/or pressure. In this context, ultrasonic bonder, thermo-mechanically bonding means and adhesives are specifically disclosed as suitable sealing means.

EP 1 088 537 (filed in 2000) discloses a highly water absorbent sheet. This absorbent sheet comprises fine cellulose fibers which provide a fibrous network holding solid super-absorbent particles in position. In order to prevent the escaping of such super-absorbent particles, the disclosed absorbent sheet relies on a hot-melt adhesive forming a further fibrous network and covering the super-absorbent particles.

WO 00/64396 (filed in 2000) discloses yet a further approach for integrity and immobilization enhancement for an absorbent member. The method comprises the application of a foamable movement obstruction agent to an absorbent member.

As to provide the desired absorbency to the article, at least the storage member will typically comprise super-absorbent material, which is admixed with the traditionally used pulp fiber material. Such super-absorbent materials can absorb many times (e.g. 10, 20 or 30 times) their own weight and are therefore very helpful when designing an article of improved fluid handling properties. Many recent products employ higher and higher concentrations of super-absorbent materials, that is concentrations in excess of 50% of the total weight of the storage member. These products achieve a high absorbing capacity with a very thin storage member and are thereby typically overall thin products. While super-absorbent materials can store very large amounts of liquid, they are often not able to distribute the liquid from the point of impact to more remote areas of the absorbent article and to acquire the liquid as fast as it may be received by the article.

Hence, the prior art has disclosed various attempts to prevent the escaping of super-absorbent particles from the absorbent core. However, especially when it comes to absorbent cores with high concentrations of super-absorbent material and the use of relatively open topsheet structures, an even more efficient prevention of the escaping of super-absorbent particles from the absorbent core is desirable.

SUMMARY OF THE INVENTION

In accordance with one aspect of the present invention, an absorbent article is provided that extends along a longitudinal axis and a transverse axis. The absorbent article includes a topsheet, a backsheet, and an absorbent core disposed between the topsheet and the backsheet. The defines a wearer facing side oriented towards a wearer when the article is being worn and an opposed garment facing side. The core includes 1) a storage layer having a wearer facing side and an opposed garment facing side, 2) a first core wrap sheet covering the wearer facing side of the storage layer, and 3) a second core wrap sheet covering the garment facing side of the storage layer. The first core wrap sheet is joined to the second core wrap sheet along at least one transverse stripe of juncture. The stripe of juncture covers a total area. The stripe of juncture provides a bond strength of at least 1 N/cm between the first core wrap sheet and a second core wrap sheet as measured as tensile strength in the longitudinal direction. The stripe of juncture comprises an open area of at least 20% of the total area.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are correspond to like reference numbers throughout, and in which:

FIG. 2 is a cross-sectional view of the disposable diaper shown in FIG. 1; and

FIG. 3 is a top plan view of the storage layer comprised by the absorbent core of a disposable diaper as shown in FIG. 1.

DETAILED DESCRIPTION OF THE INVENTION

Definitions

Figure 1:
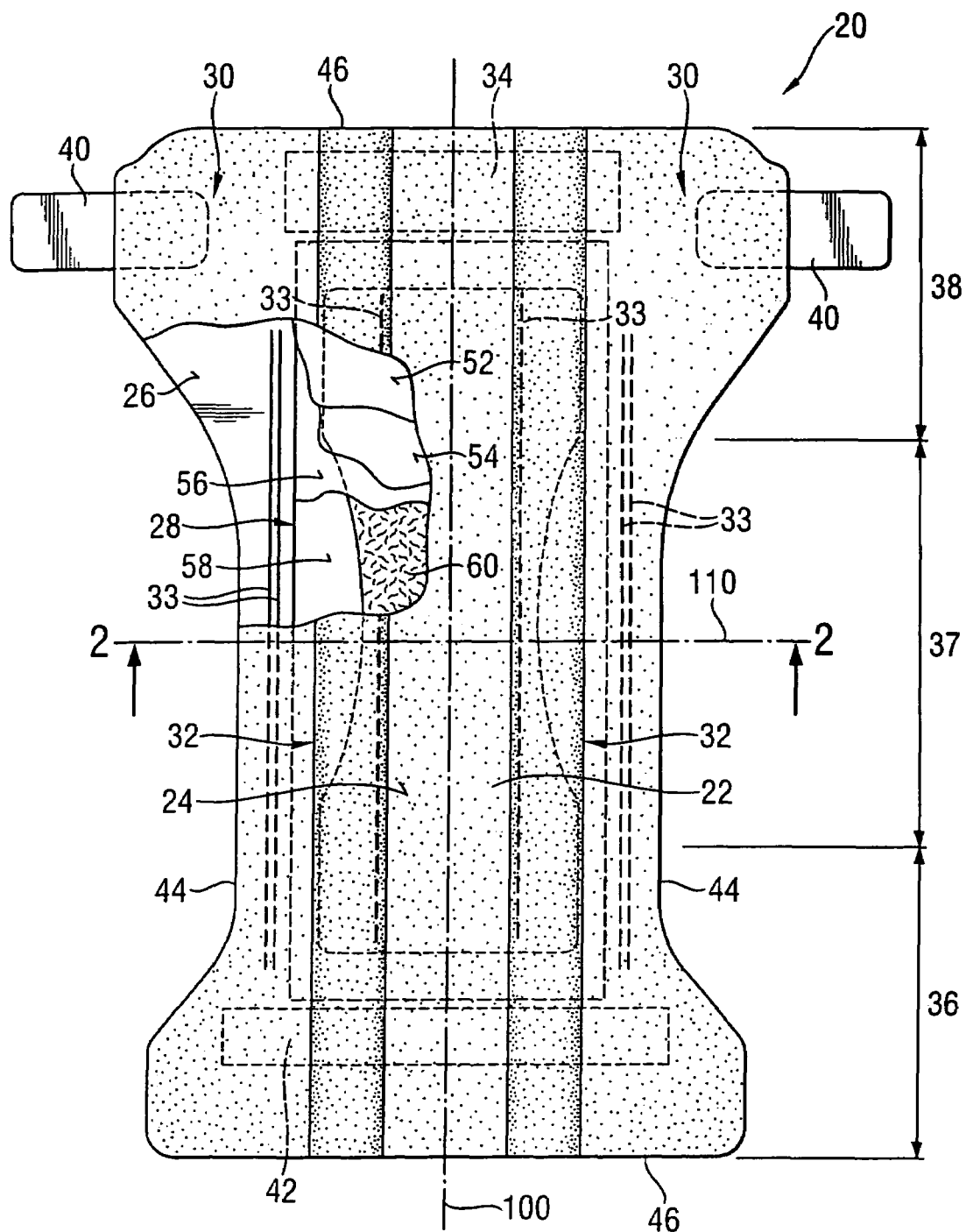
FIG. 1 is a top plan view of a disposable diaper, with the upper layers partially cut away.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

The terms "thickness" and "caliper" are used herein interchangeably.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven", "nonwoven fabric" and "nonwoven web" are used interchangeable.

The disposable article 20 has two centerlines, a longitudinal centerline 100 and a transverse centerline 110.

The term "longitudinal", as used herein, refers to a line, axis or direction in the plane of the disposable article 20 that is generally aligned with (e.g., approximately parallel to) a vertical plane which bisects a standing wearer into left and right body halves when the disposable article 20 is worn.

The terms "transverse" or "lateral" as used herein, are interchangeable, and refer to a line, axis or direction which lies in the plane of the disposable article 20 that is generally perpendicular to the longitudinal direction.

Absorbent Articles

FIG. 1 is a plan view of a diaper 20, illustrated in accordance with one embodiment of an absorbent article according to the present invention, is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis preferably further includes side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 preferably attached to the rear waist region 38 and a landing zone 42 attached to the front waist region 36. The diaper 20 has a longitudinal axis and centerline 100 and a transverse axis and centerline 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 preferably attached to the rear waist region 38. In a preferred embodiment the fastening system further comprises a landing zone 42 attached to the front waist region 36. The fastening member is attached to the front waist region 36, preferably to the landing zone 42 to form leg openings and an article waist.

Diapers 20 constructed in accordance with certain aspects of the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core preferably comprises an acquisition system 50, which comprises an upper acquisition layer 52 facing towards the wearer and a lower acquisition layer 54. In one preferred embodiment the upper acquisition layer comprises a nonwoven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer 60.

The storage layer 60 is preferably wrapped by a core wrap material. In one preferred embodiment the core wrap material comprises a first core wrap layer 56 (top layer) and a second core wrap layer 58 (bottom layer). The first core wrap layer 56 and the second core wrap layer 58 can be provided from a non-woven material. One preferred material is a so-called SMS material, comprising a spunbonded, a melt-blown and a further spunbonded layer. The first core wrap layer 56 and the second core wrap layer 58 may be provided from two or more separate sheets of materials or they may be alternatively provided from a unitary sheet of material. Such a unitary sheet of material may be wrapped around the storage layer 60, e.g. in a C-fold. The first core wrap layer 56 and the second core wrap layer 58 may also be joined to each other, preferably along their periphery. In one preferred option both layers are joined along their longitudinal peripheries, in other embodiments they are joined along the transversal peripheries, or along the longitudinal and the transversal peripheries. The joining can be achieved my multiple means well known in the art, eg. by adhesive means, using a continuous or a discontinuous pattern, and preferably a linear or curvilinear pattern.

The storage layer 60 typically comprises fibrous materials, mixed with superabsorbent, absorbent gelling materials. Other materials described above as suitable for the absorbent core 28 may also be comprised. Exemplary storage layers can comprise a superabsorbent material in an amount corresponding to at least 30%, or at least 40%, or at least 50%, or at least 60%, or at least 70%, or at least 80% or at least 90% of the total weight of the storage layer.

A upper liquid acquisition layer 52 useful in a diaper can comprise any of the non-woven fabrics described below. A preferred liquid acquisition layer 52 comprises a binder comprising a styrene-butadiene latex binder. Preferably, the styrene-butadiene latex binder has a carboxylation level of at least 10%, preferably at least 12%. Preferably, the upper liquid acquisition layer 52 comprises polyester fibers and the liquid acquisition layer comprises 20 to 40 weight percent of styrene-butadiene latex binder, and 60 to 80 weight percent of said polyester fibers. Even more preferably, the polyester fibers comprise 20 to 80 weight percent of a first type of fibers, and 20 to 80 weight percent of a second type of fibers, the second type of fibers comprising spiral-crimp fibers. Highly preferred are upper liquid acquisition layers wherein the first type of fibers exhibits a flat crimp and wherein the second type of fibers comprises hollow chemically homogeneous bi-component fibers. Also highly preferred are any upper liquid acquisition layers wherein the polyester fibers are carded to form a nonwoven.

Preferred acquisition systems may also comprise superabsorbent materials. Such acquisition systems may also comprise a single acquisition layer or multiple acquisition layers. Where multiple acquisition layers are comprised any of these layer may comprise superabsorbent materials. Such superabsorbent material may be comprised in an amount corresponding to at least 30%, or at least 50% or at least 70%, at times even in an amount of 100% of the total weight of the respective acquisition layer.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibres may be of natural or man-made origin. They may be staple or continuous filaments or be formed in situ.

Nonwoven fabrics can be formed by many processes such as meltblowing, spunbonding, carding. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Example synthetic fibers, which are derived from natural fibers, include but are not limited to rayon and lyocell, both of which are derived from cellulose, a natural polysaccharide fiber. Synthetic fibers, which are not derived from natural fibers, can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers, which can be laid into webs at a distinctly subsequent point in time. Example direct extrusion processes include but are not limited to: spunbonding, meltblowing, solvent spinning, electrospinning, and combinations thereof typically forming layers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermobonding by use of heated calendar rolls.

Preferred Topsheets

Exemplary topsheets can be compliant, soft feeling, and non-irritating to the wearer's skin. Further, the topsheet 24 should be liquid pervious, permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 28. Alternatively, the topsheet 24 may be surfactant treated to make it hydrophilic.

The topsheet 24 preferably has a plurality of apertures with an effective aperture size of at least 0.2 square millimeters, more preferably, the plurality of apertures have an effective aperture size of at least 0.5 square millimeters, even more preferably, the plurality of apertures have an effective aperture size of at least 1.0 square millimeters, and most preferably, the plurality of apertures have an effective aperture size of at least 2.0 square millimeters. Effective apertures are those which have a gray level of 18 or less on a standard gray level scale of 0-255, under the image acquisition parameters described in EP 1 032 336 B1. An aperture having a material free area of x square millimeters is to be understood as having an effective aperture size of at least x square millimeters.

The topsheet 24 preferably has an effective open area of at least 15 percent, more preferably the topsheet has an effective open area of at least 20 percent, even more preferably, the topsheet has an effective open area of at least 25 percent, and most preferably the topsheet has an effective open area of at least 30 percent. Preferably, at least 50% or at least 75% of the topsheet surface are provided with such apertures.

Preferred Absorbent Cores

All of the above described fibers and manufacturing techniques can be useful for providing core wrap sheets in accordance with the principles of the present invention.

Preferred core wrap sheets are made of a hydrophilic material to promote rapid transfer of liquids (e.g. urine) through at least the first core wrap sheet. If such core wrap sheets are made of a hydrophobic material, such material can be treated to be hydrophilic, for example by treatment with a surfactant.

There are multiple ways to envelope an absorbent core using a first core wrap sheet and a second core wrap sheet, all of which are within the scope of the present invention. For example, two separate wrap sheets may be used, the first core wrap sheet covering the wearer facing side of the core and the second core wrap sheet covering the garment facing sided of the core. Both wrap sheets can then be joined along longitudinally extending stripes of juncture, one stripe of juncture to each side of the absorbent core. Alternatively, the first core wrap sheet can be integral with the second core wrap sheet and be provided from one and the same sheet of material. Then, only one longitudinally extending stripe of juncture needs to be employed as to achieve the enveloping. Such stripe of juncture can either be of the wearer facing side of the core, or on the garment facing side of the core on either lateral side of the core. The overlapping ends of the wrap sheet material, which are to be joined by said stripe of juncture, can be arranged as to create a butt seal or can be arranged as to create an overlapping seal. Both an overlapping seal and a butt seal can be joined using a stripe of juncture in accordance with certain aspects of the present invention.

The core wrap sheets (if present) can be not only joined by a longitudinally extending stripe of juncture (for example a side seal), but also by a transversally extending stripe of juncture, which is typically positioned either at the front end of the absorbent core or at the rear end of the absorbent core or at both ends of the absorbent core. Such a transversally extending stripe of juncture can be provided by the same means as a longitudinally extending stripe of juncture.

The stripe of juncture 72 may comprise different elements having a bonding function, herein referred as bonding elements. For example, bonding elements can be provided by adhesive bonding, by thermo-mechanical bonding, by ultrasonic bonding and the like. The area of a rectangle comprising all bonding elements of the stripe of juncture 72 is herein referred to as the total area of the stripe of juncture 72. According to the present invention, however, the stripe of juncture also comprises an open area. Open area, as used herein, denotes an area where no bonding elements are present.

In one preferred embodiment of the present invention, which is shown in FIG. 3, the bonding elements are threads of adhesives. These threads are preferably created by slot coating, but can also be provided by spray application. The plurality of threads is separated by a plurality of areas comprising no adhesive. The threads preferably have a width of 0.5 mm to 2 mm, most preferably of 1 mm and the areas comprising no adhesive preferably have a width of 0.5 mm to 2 mm, most preferably of 1 mm. When both areas have the same width, the stripe of juncture 72 has an open area of 50% of the total area.

Generally, in accordance with the present invention, stripes of juncture 72 having an open area of at least 20%, or at least 30%, or at least 40%, or at least 50%, or at least 60%, or at least 70%, or at least 80%, or at least 90% of their total area are preferred. However, the open area should not be more than 95% of the total area as to ensure reliable bonding.

Preferably, as to achieve sufficient macroscopic bond strength the threads of adhesive have a diameter of more than 100 micrometer, more preferably of more than 250 or 500 micrometer.

Core wrap sheets according to the present invention are preferably provided in the form of non-woven webs. More preferably, they are provided from polyolefin, more preferably from polypropylene. Preferred core wrap sheets have a basis weight from 3 gram per $m^2$ to 50 gram per $m^2$, more preferably from 5 gram per $m^2$ to 30 gram per $m^2$, preferably from 8 gram per $m^2$ to 15 gram $m^2$.

The stripe of juncture will provide certain bond strength between the core wrap sheets. The stripe of juncture will have its largest extension in a first direction. The bond strength between the core wrap sheets, as used herein, is to be understood as the tensile strength in a second direction which is perpendicular to the first direction and within the plane defined by the core wrap sheets. To test tensile strength a test specimen of 2.54 cm (1 inch) width is cut at a representative (typically central) position by two cutting lines oriented in the second direction. Tensile strength is then measured using this test specimen of material in accordance with ASTM method D 1876-01, which is modified as follows: The specimen length is 60 mm and unbonded ends of 10 mm length are used for clamping in the grips of the testing machine (see paragraph 5.2 of D 1876-01). The portions of the first and second core wrap sheet forming part of the specimen are used as flexible adherends (see paragraph 5.1 of D 1876-01). Further, tensile strength is reported (in units of Newton divided by centimeter specimen width; N/cm) as the maximum value of the obtained autographic curve (see paragraph 8.1 of D 1876-01).

According to the present invention the stripe of juncture 72 provides a bond strength of at least 0.5 N/cm between the first core wrap sheet 56 and a second core wrap sheet 58 as measured as tensile strength in the longitudinal direction. Preferably the stripe of juncture 72 provides a bond strength of at least 1.0 N/cm or 1.5 N/cm or 2 N/cm or 3 N/cm.

Without wishing to be bound by theory, it seems particularly beneficial to have stripes of juncture which comprise relatively large open areas. It appears that the occurrence of the gel-on-skin phenomenon is in part caused by super-absorbent particles which in the process of manufacturing are captured within such a line of junction. When a stripe of juncture is provided by continuous adhesive application, the superabsorbent material is limited in its ability to swell by being confined by the adhesive providing the stripe of juncture. However, the super-absorbent particle is likely to swell once the article is in use and receives liquid. When this swelling is highly restricted by the presence of adhesive, the swelling forces are typically high enough to allow swelling in the direction of the core wrap sheets. These core wrap sheets are typically provided by non-woven materials or tissue materials or similar materials which are relatively week. Hence, wherever the stripe of juncture itself does not provide sufficient open area to accommodate the swelling of super-absorbent particles, such particles will expand in the direction of the core wrap sheets. Therefore, they are likely to escape through the core wrap sheets, often also causing damage to the core wrap sheets. This escaping of super-absorbent material from the core and especially out of the areas of the stripes of juncture appears to noticeably contribute to occurrences of gel-on-skin. If, however, in accordance with the present invention a stripe of juncture comprising a sufficiently high open area is provided, this adhesive application will lead to more room for swelling within the stripe of juncture. The adhesive will either find a sufficient open area within the stripe of juncture to allow for swelling without exerting any pressure against the wrap sheets and against surrounding adhesive material or surrounding adhesive material will be elastic enough as to allow for swelling within the stripes of juncture while no or very little pressure is exerted towards the core wrap sheets.

In view of these considerations it seems best to select the dimension of the bonding elements and of the areas free of bonding elements in view of the size of the superabsorbent particles which could escape from the absorbent core 28. The value to be considered specifically is the mean diameter of the super-absorbent particles.

The mean diameter is to be determined using EDANA method 420.2-02 entitled "Particle size distribution". This EDANA method is a sieving method and reports the mass fraction in percent for each particle size fraction remaining on the different sieves employed. Based on this report the mean diameter is calculated according to ASTM test method D 1921-96, namely paragraph 13 thereof entitled "Analysis of Particle Distribution".

The smallest dimension of the bonding elements should be at least 0.2 times the mean diameter of the super-absorbent material ("MD"). Preferably the smallest dimension of the bonding elements is from 0.2 to 3 times the MD, more preferably from 0.5 to 2 times the MD, most preferably from 0.8 to 1.2 times the MD. The bonding elements are then large enough to create the macroscopically desirably bond strength and also large enough to reliably capture and retain particles of super-absorbent materials which in the production process are entrapped by the bonding elements. On the other hand, they do not unnecessarily restrict the available open area.

The smallest dimension of the open areas should be at least 0.5 times the MD, preferably is from 0.5 to 10 times the MD, more preferably from 1 to 5 times the MD. The open areas are then large enough to allow for relatively unrestricted swelling of the superabsorbent particles.

Hence, the stripes of juncture 72 according to the present invention provide a sufficient bond strength on a macro level (when looking at the performance of the overall absorbent article), but at the same time sufficient weakness and swelling space on a micro level (when looking at the environment of single particles of super-absorbent material).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
   a longitudinal axis;
   a transverse axis;
   a topsheet;
   a backsheet; and
   an absorbent core disposed between the topsheet and the backsheet, wherein the absorbent core includes:
      a first core wrap sheet;
      a second core wrap sheet
      a storage layer, including superabsorbent particles, disposed between the first core wrap sheet and the second core wrap sheet; and
      at least one stripe of juncture joining the first core wrap sheet to the second core wrap sheet,
   wherein the stripe of juncture includes a plurality of bonded areas that are separated from each other by a plurality of unbonded areas, wherein each of the unbonded areas is open to the storage layer, wherein the stripe of junction defines a total area, the plurality of unbonded areas defines an open area, and the open area is at least 20% of the total area.

2. The disposable absorbent article of claim 1, wherein the open area is from about 30% to about 95% of the total area.

3. The disposable absorbent article of claim 1, wherein the plurality of bonding elements are provided by thermo-mechanical bonding.

4. The disposable absorbent article of claim 1, wherein the open area is at least 50% of the total area.

5. The disposable absorbent article of claim 1, wherein each of the unbonded areas has a width that is 0.5 to 2 millimeters.

6. The disposable absorbent article of claim 1, wherein the superabsorbent particles have a mean diameter, and each of the unbonded areas has a width that is 0.5 to 10 times the mean diameter.

7. The disposable absorbent article of claim 1, wherein the superabsorbent particles have a mean diameter, and each of the unbonded areas has a width that is 1 to 5 times the mean diameter.

8. The disposable absorbent article of claim 1, wherein each of the bonded areas has a width that is 0.5 to 2 millimeters.

9. The disposable absorbent article of claim 1, wherein the superabsorbent particles have a mean diameter, and each of the bonded areas has a width that is 0.2 to 3 times the mean diameter.

10. The disposable absorbent article of claim 1, wherein the superabsorbent particles have a mean diameter, and each of the bonded areas has a width that is 0.5 to 2 times the mean diameter.

11. The disposable absorbent article of claim 1, wherein the superabsorbent particles have a mean diameter, and each of the bonded areas has a width that is 0.8 to 1.2 times the mean diameter.

12. The disposable absorbent article of claim 1, wherein the plurality of bonding elements are provided by adhesive bonding.

13. The disposable absorbent article of claim 1, wherein the plurality of bonding elements are provided by ultrasonic bonding.

14. The disposable absorbent article of claim 1, wherein the plurality of bonding elements are disposed in a linear pattern.

15. The disposable absorbent article of claim 1, wherein:
   the core wrap has a transverse periphery; and
   the stripe of juncture joins the first core wrap sheet to the second core wrap sheet along the transverse periphery.

16. The disposable absorbent article of claim 1, wherein:
   the core wrap has a first transverse periphery and a second transverse periphery;
   the stripe of juncture is a first stripe of juncture, the plurality of bonded areas is a first plurality of bonded areas, the plurality of unbonded areas is a first plurality of unbonded areas, the total area is a first total area, and the open area is a first open area;
   the first stripe of juncture joins the first core wrap sheet to the second core wrap sheet along the first transverse periphery; and
   a second stripe of juncture joins the first core wrap sheet to the second core wrap sheet along the second transverse periphery, wherein the second stripe of juncture includes a second plurality of bonded areas that are separated from each other by a second plurality of unbonded areas, wherein each of the unbonded areas is open to the storage layer, wherein the second stripe of junction has a second total area, the second plurality of unbonded areas defines a second open area, and the second open area is at least 20% of the second total area.

17. The disposable absorbent article of claim 1, wherein:
the core wrap has a longitudinal periphery; and
the stripe of juncture joins the first core wrap sheet to the second core wrap sheet along the longitudinal periphery.

18. The disposable absorbent article of claim 1, wherein:
the core wrap has a first longitudinal periphery and a second longitudinal periphery;
the stripe of juncture is a first stripe of juncture, the plurality of bonded areas is a first plurality of bonded areas, the plurality of unbonded areas is a first plurality of unbonded areas, the total area is a first total area, and the open area is a first open area;
the first stripe of juncture joins the first core wrap sheet to the second core wrap sheet along the first longitudinal periphery; and
a second stripe of juncture joins the first core wrap sheet to the second core wrap sheet along the second longitudinal periphery, wherein the second stripe of juncture includes a second plurality of bonded areas that are separated from each other by a second plurality of unbonded areas, wherein each of the unbonded areas is open to the storage layer, wherein the second stripe of junction has a second total area, the second plurality of unbonded areas defines a second open area, and the second open area is at least 20% of the second total area.

19. The disposable absorbent article of claim 1, which is a diaper.

* * * * *